US007831084B2

(12) United States Patent
Saviharju

(10) Patent No.: US 7,831,084 B2
(45) Date of Patent: Nov. 9, 2010

(54) CONTROL OF A RECOVERY BOILER OR ALIKE

(75) Inventor: Kari Saviharju, Espoo (FI)

(73) Assignee: Andritz Oy, Helsinki (FI)

( * ) Notice: Subject to any disclaimer, the term of this patent is extended or adjusted under 35 U.S.C. 154(b) by 858 days.

(21) Appl. No.: 11/718,008

(22) PCT Filed: Jul. 11, 2005

(86) PCT No.: PCT/FI2005/000327

§ 371 (c)(1),
(2), (4) Date: Apr. 26, 2007

(87) PCT Pub. No.: WO2006/048495

PCT Pub. Date: May 11, 2006

(65) Prior Publication Data

US 2009/0139468 A1    Jun. 4, 2009

(51) Int. Cl.
*G06K 9/00* (2006.01)
(52) U.S. Cl. .................... 382/141; 382/260; 110/185
(58) Field of Classification Search ................ 382/100, 382/141, 154, 191, 206, 260, 312; 110/185
See application file for complete search history.

(56) References Cited

U.S. PATENT DOCUMENTS 3,847,092 A * 11/1974 Gilbert ................... 110/101 R (Continued)

FOREIGN PATENT DOCUMENTS

JP    63-188749    8/1988

(Continued)

OTHER PUBLICATIONS

International Search Report mailed Jan. 31, 2006.

*Primary Examiner*—Matthew C Bella
*Assistant Examiner*—Shervin Nakhjavan
(74) *Attorney, Agent, or Firm*—Nixon & Vanderhye P.C.

(57) ABSTRACT

Method and system for controlling the operation of a recovery boiler or another boiler having a furnace wherein the operation is monitored by monitoring sensors, the sensors converting the acquired electromagnetic radiation to electrical signals which are conducted to image processing which forms an image of an object, such as the char bed and/or the char and/or chemicals on the furnace walls and/or deposits on boiler surfaces, based on the data from the sensors, and wherein the operation, such as burning of the char bed and/or the formation of char and/or chemicals on the furnace walls and/or the formation of deposits on boiler surfaces, is controlled with help of the image, wherein the sensors are arranged to produce sensor signals for 3D (three-dimensional) imaging, wherein the sensor signals are conducted to the image processing unit for forming a 3D image, such as an image of the bed and/or the char and/or the chemicals, and/or its shape describing derivatives, and/or temperature chart of the bed surface, and wherein the image processing further comprises a filtering phase wherein the sensor signals or the 3D image are/is filtered in order to avoid the thermal radiation emission of hot gases, liquids and/or particles in the furnace, wherein the sensor signals or the 3D image are/is conducted to a filter unit filtering the signals/images to several relatively narrow bands (BAND1 to BANDn), whereby the final 3D image is obtained by comparative analysis of the sensor signals or the 3D images from the chosen different frequency bands.

34 Claims, 2 Drawing Sheets

U.S. PATENT DOCUMENTS

| | | | |
|---|---|---|---|
| 4,110,617 A * | 8/1978 | Legille | 250/342 |
| 4,539,588 A * | 9/1985 | Ariessohn et al. | 348/164 |
| 5,010,827 A * | 4/1991 | Kychakoff et al. | 110/185 |
| 5,225,883 A * | 7/1993 | Carter et al. | 356/45 |
| 5,724,895 A * | 3/1998 | Uppstu | 110/238 |
| 6,909,816 B2 * | 6/2005 | Kychakoff et al. | 382/285 |
| 2007/0002467 A1 * | 1/2007 | Claytor | 359/743 |
| 2008/0298426 A1 * | 12/2008 | Koschack et al. | 374/7 |

FOREIGN PATENT DOCUMENTS

JP     2003-050274     2/2003

\* cited by examiner

CONTROL OF A RECOVERY BOILER OR ALIKE

CROSS RELATED APPLICATION

This application is the US national phase of international application PCT/FI2005/000327 filed 11 Jul. 2005 which designated the U.S. and claims benefit of Finnish patent application FI 20041419 filed 4 Nov. 2004, the entire contents of these applications are incorporated by reference.

FIELD OF INVENTION

The present invention relates to a method and System for controlling the operation of a recovery boiler or another boiler having a furnace wherein the operation is monitored by monitoring sensors, said sensors converting the acquired electromagnetic radiation to electrical signals which are conducted to image processing unit which forms an image of an object.

The present invention relates especially to a method for controlling the char bed in a recovery boiler wherein the char bed is monitored by monitoring sensors, said sensors converting the acquired radiation to electrical signals which are conducted to an image processing unit which forms an image of the char bed based on the data from the sensors, and wherein the char bed is controlled with help of the image formed in the image processing unit.

BACKGROUND OF THE INVENTION

In the Kraft pulp production process, a fibrous material, most commonly wood chips, is broken down into pulp in a digester under pressure in a steam-heated aqueous solution of sodium hydroxide and sodium sulphide, called white liquor. After cooking in the digester, the pulp is separated from the residual liquid called black liquor. Black liquor is an aqueous solution containing wood lignins, other organic material, and inorganic compounds oxidized in the digester during the cooking process. It is dried in the evaporation plant to 55-85% dry solids concentration (concentrated) and then black liquor 2 is sprayed (3) into the furnace 1 of the recovery boiler, and burned (in a recovery boiler) to recover cooking chemicals (FIG. 1), and generate steam, which is used in the pulp mill for power generation, for pulp cooking and drying, for black liquor drying, and for other energy requirements.

The inorganic material in black liquor is recovered in the recovery boiler for reuse in the cooking process. This recovery requires special, reducing atmosphere in the lower furnace. Typically this is achieved by creating a char bed 4 on the floor 10 of the furnace. The shape and size of the char bed depend on boiler design, but it can be 1-2 meters high at the highest spot, calculated from the smelt overflow height 15. The inorganics are taken out from the recovery boiler furnace as molten smelt 16a and 16b, the main compounds in smelt being typically $Na_2CO_3$ and $Na_2S$, with smaller smaller amounts of potassium based compounds. Smaller amount of non-process elements are also flowing out from the furnace in the smelt.

Liquor is sprayed into the furnace from several locations 3, which are called ports. The ports are typically located on one level, called liquor feed level, but there can be also more levels to meet special requirements. When liquor is sprayed into the furnace, it heats up due to hot atmosphere, which result in drying and in pyrolysis. In the pyrolysis phase the organic structure of black liquor is destroyed; part of the material will end as pyrolysis gas into the furnace atmosphere, and part of the material passes further as char. Both material streams ignite and burn, until the organic material has been consumed. Only a very small part of the original organic material in black liquor leaves the furnace as unburned in modern recovery boilers. Depending on the original droplet size, the char burns totally in flight, or end into the char bed 4, and onto furnace walls. In modern recovery boilers drying, pyrolysis and combustion on furnace walls should be minimized. The char bed is formed of burning liquor droplets 12, burning char and inorganic material, in which sulphur compounds are reacting from oxidized form to reduced form. This reduction requires the presence of carbon, and thus the char bed control is essential for achieving good reduction efficiency. The reduction efficiency expresses which share of total sulphur in smelt, flowing from the furnace 16a, 16b, is in reduced form, i.e. as $Na_2S+K_2S$. Typically this is over 90%. When reduction is good the reduction efficiency is over 95-96%.

Small liquor droplets are also generated during liquor spraying, and these droplets 13 dry, pyrolyze and burn in flight. The droplets, finally entering the floor area of the furnace, tend to contain oxidized sulphur due to the combustion atmosphere in the upper furnace. Then again carbon is needed for sulphur reduction. The good total reduction requires good carbon coverage over the whole floor. The reactions between carbon and oxidized sulphur, the most important of which is, $Na_2SO_4$, are strongly temperature-dependent, and require energy. Thus only a relatively thin surface layer 14 on the surface of the char bed 4 is active, which means that the char bed does not have to be high. Controlling possibilities and characteristics of liquor spraying and different combustion air feeds, together with the reduction characteristics, dictate in practice the shape of the char bed. If the bed grows too big, there is a risk of bed falling into airports, typically into primary airports, and a risk of smelt escaping via smelt spouts into the dissolving tank or into dissolving tanks.

An effective burning process requires that the char bed can be controlled reliably. Thus a need to monitor and control the size and shape of the char bed in a Kraft recovery system has been recognized for many years; however, no reliable technique for controlling the char bed automatically has yet been available.

Gas temperatures in the furnace range typically from 100-200 degree C. which is the temperature of incoming air and liquor to 1200-1400 degree C. in the hottest areas of the furnace, which is for instance the area, where tertiary air is fed into the furnace, or where final combustion takes place. On the char bed surface the temperature is typically 900-1200 degree C. The temperature of the smelt exiting the furnace is typically 800-900 degree C. The clean walls 8 of the furnace have a temperature of 250-400 degree C., depending on the pressure of the boiler and on the observation point; tube or the fin between the tubes, which has higher temperature than the tube, inside which evaporating water flows, cooling the furnace walls and generating the main portion of steam for superheating in super heaters. Deposition takes typically place on furnace walls, which raises the surface temperature of the deposit closer to temperatures in the gas phase and in the char bed.

All the surfaces radiate thermal radiation. This radiation is basically continuous, but changes in radiation properties, such as emissivity, as the function of temperature causes that the radiation intensity distribution does not follow the Planck's law. Naturally, when the dependency of the radiation properties as the function of the temperature and composition is known, proper correction factors can be generated to fit the measured intensities on several wavelengths, to estimate the surface temperature of the radiating surface.

Gases, liquids and solids in the furnace gas atmosphere radiate as well, but this radiation is concentrated, at least partly, to spectrums; and there may be areas in the wavelengths, where radiation or absorption is weak. These windows are potential for imaging the char bed. The small particles in the furnace radiate and scatter incoming electromagnetic radiation, complicating the system. Thus the electromagnetic radiation phenomena in the furnace are very complex. The key factor to be able to image the char bed from the hot gas atmosphere around, with vapours and particles, is to receive electromagnetic radiation information from the char bed, which is not excessively influenced by the surrounding atmosphere.

It is known to use a TV camera mounted in a special port or into an air inlet port to monitor the bed, i.e. the TV camera continuously scans electromagnetic information from the bed and a TV set provides a picture in the control room so that the operator may use this picture to control the furnace. The detector of this type camera operates today typically around 1.7 micro meter wavelength.

Such a means for monitoring the bed height and shape with TV cameras and having the capability of automatically reacting when the bed deviates beyond the limit from a preset height and/or shape and to control furnace operating parameters to maintain the bed at the required height and/or shape has been disclosed in CA 1166842. The recovery boiler is provided with ports to mount the TV cameras, or the cameras may be mounted in selected airports. The signal from these cameras is carried via lines to a television monitor that visually displays the picture of the bed taken by each of the cameras on a monitoring screen in the control room. The signal is also carried to a video image processor which digitizes the images sensed by each of the cameras coding each point of each frame based on shade or greyness or brightness to permit an analyzer built into the image processor to discriminate between the different shades and thereby obtain the interference between the char bed and the surrounding atmosphere. In this manner the location of the interface and thus the outline of the bed are determined.

While a camera responsive to visible radiation may be used, the fume particles and gaseous radiation cause problems in the visible region and the intensity of infrared emissions from the process area will be greater than emissions in the visible portion of the spectrum. Further, environmental factors related to the process environment may interfere with infrared emissions less than visible emissions. For these reasons, an infrared camera, as disclosed for example in U.S. Pat. No. 5,219,226, may be used to produce a video image representative of the intensity of received infrared radiation.

An disadvantage of the prior art solutions using conventional TV or IR (infrared) cameras is that they are only able to form a plane (2D) view of the char bed which cannot provide a reliable image for control purposes.

Some efforts have been made to obtain a more reliable image of the char bed. JP-A-61130725 discloses a char bed monitoring device wherein a TV camera and image processing device are provided for picking up the char bed and for forming a three dimensional image of the char bed by means of an image signal. However, in this JP publication the TV camera produces a conventional 2D image signal, and the 3D image is afterwards achieved by image data processing with help of the plane view information. This requires a lot of data processing capacity and is not a suitable system for forming a 3D image of the char bed for control purposes.

A further disadvantage of the prior art solutions is that they operate only at a certain wavelength range. The prior art systems thus use optical filters to limit the wavelength of electromagnetic radiation transmitted from the bed to be imaged, typically to wavelengths greater than 1 micro meter. Typically the filter limits the transmitted light to a narrow band, as disclosed for example in U.S. Re. 33,857.

SUMMARY OF THE INVENTION

It is therefore an object of the present invention to eliminate the disadvantages of the prior art and to provide an improved method and System for controlling the operation of a recovery boiler or another boiler.

It is further an object of the present invention to provide a method to automatically control the char bed by controlling the spraying of the black liquor, and the feeds of combustion air by means of the image information.

The present invention is based on the system using 3D sensor arrangement, whereby a real time 3D image of the char bed can be retrieved and processed for control purposes. Further, the present invention is based on use of several wavelength ranges in the imaging, such as char (smelt) bed imaging. The same invention can be used in imaging build-up formation of char or chemicals onto furnace walls.

Characteristic features of the present invention are in detail presented in the enclosed claims.

The advantages of the present invention are the following: The interferences and the char bed can be easily separated in the imaging process by comparing the 2D or/and 3D images from different wavelengths, and finding the correlations. Further, a reliable image of the char bed can be attained. And still further a char bed surface temperature chart can be constructed by fitting the measured radiation intensities on several wavelengths to the Planck's radiation intensity distribution curve. And still further, a static black liquor burning process can be modified so that it becomes a dynamically controlled process with shorter control response times.

BRIEF DESCRIPTION OF DRAWINGS

The foregoing, and additional objects, features and advantages of the present invention will be more clearly understood from the following detailed description of preferred embodiments of the present invention, taken in conjunction with accompanying drawings, in which.

DETAILED DESCRIPTION OF PREFERRED EMBODIMENTS

Figure 1:
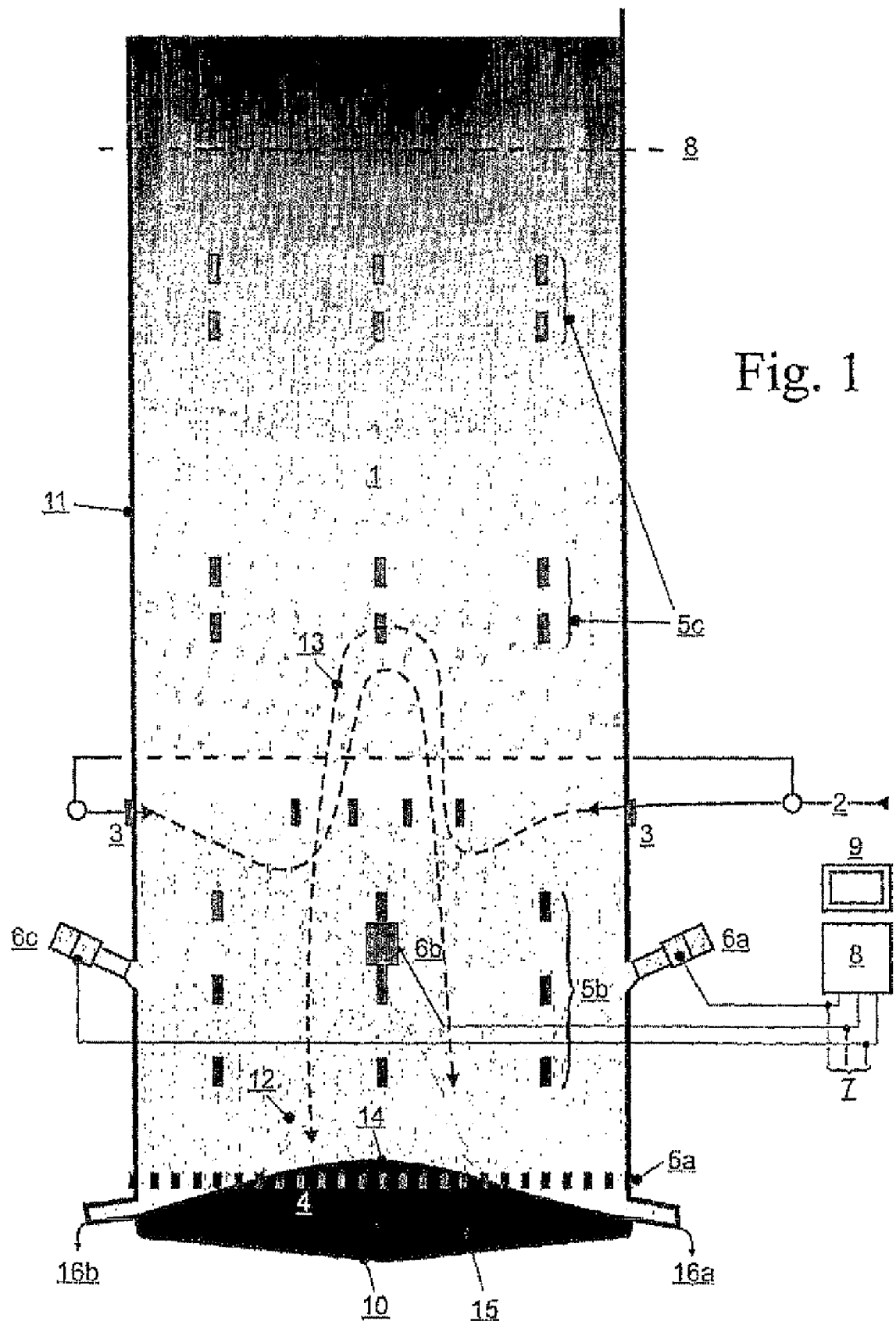
FIG. 1 is a schematic cross section figure of a recovery boiler according to the present invention.

FIG. 1 presents a recovery boiler furnace 1 in a Kraft pulp production process for burning black liquor. Black liquor 2 discharged in a digestion process is injected into the boiler through injection nozzles 3 arranged in the furnace 1. It forms a char bed 4 over the floor 10, at the bottom of the furnace 1, and the bed is burnt by introducing combustion air into the furnace of the boiler through air inlet openings 5a, 5b and 5c arranged in different heights (primary openings 5a, secondary openings 5b in the lower part and tertiary openings 5c in the middle part of the furnace 1, and in low NOx combustion cases tertiary openings also in the upper part of the furnace 1).

The char bed is monitored by 3D imaging for example with three sensors 6a to 6c arranged around the boiler as seen in FIG. 1. The signals from these sensors are carried via lines 7 to a control unit 8 for image processing. The control unit processes the signals and produces a 3D image of the char bed, which can be visually displayed on a monitoring screen 9 in the control room. The operator may use this image to manually control the furnace and thus the size and form of the char bed.

Figure 2:
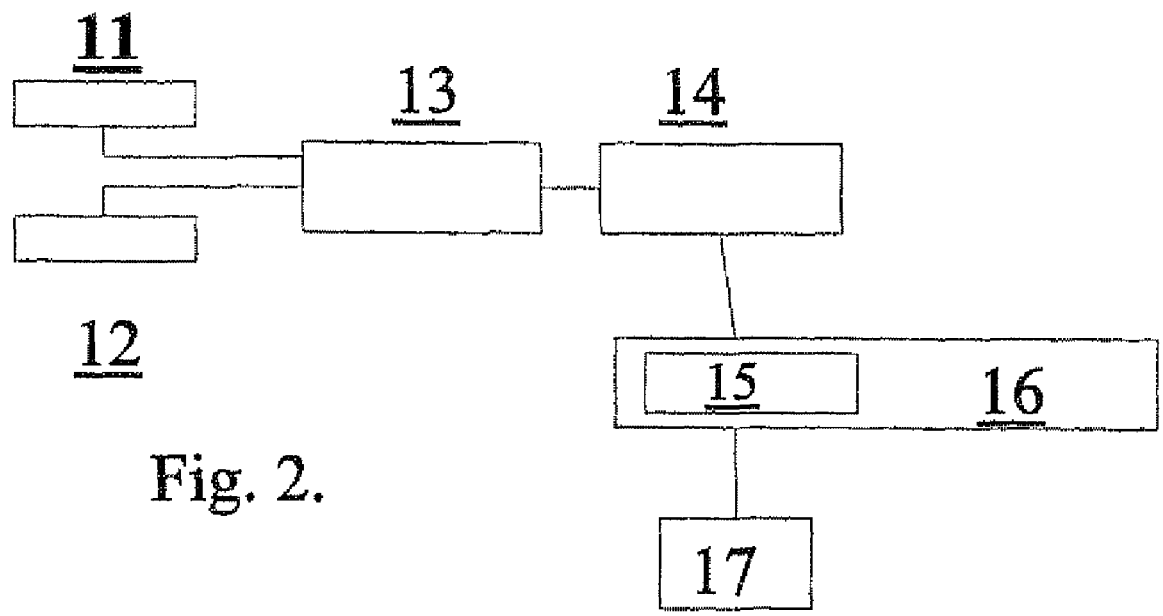
FIG. 2 is a detailed block diagram of the char bed control system according to the present invention.

FIG. 2 shows the block diagram of the present invention. The image sensors 6a to 6c are 3D sensors consisting of two adjacent sensor heads 11 and 12 capable of forming a stereo image of the char bed in order to define a position off each point on the surface of the char bed and thus capable to produce 3D imaging signals for the image processing in the control unit. In practice the surface 14 of the char bed 4 is divided into elements, the number of which depends on the number of cells in the sensors. For instance in a furnace with a cross section of 15 meters×14 meters, 0.1 m×0.1 m element size requires 21 000 cells under ideal conditions. Further the sensor heads 11, 12 are wide range wavelength sensors capable of deriving image signals from a wide range including several spectral windows, for example as shown in U.S. Re, 33,857, FIG. 2, according to which spectral windows generally suitable for char bed imaging identified by the above analysis include the following: 1.57 to 1.73 micrometers; 2.23 to 2.43 micrometers; 3.25 to 4.05 micrometers; 4.80 to 5.30 micrometers; 6.90 to 7.20 micrometers; 7.60 to 7.80 micrometers; 7.90 to 13.90 micrometers, and also other windows beyond 13.90 micrometers to millimeter or sub-millimeter wavelength range. The spectral windows can also include ultraviolet and visible wavelength range. Physically the sensor heads may be integrated for all the used wavelengths, or divided into several sectors. The sectors can be even physically separate; i.e. sensor heads are separate for different wavelengths used in the system for imaging.

The sensors in the sensor heads 11, 12 are constructed so that they are sensitive to signals at the certain wavelengths, which have been chosen so that the combustion processes in the furnace, and the atmosphere in the furnace between the char bed and the sensors disturbs the signals originating from the char bed as little as possible. An example is the superconducting antenna-coupled micro bolometer, or the quantum well. The received signals at different wavelengths are conducted to the image processing control unit 14 for forming a 3D image of the bed, which can then be displayed on the screen but the image can also be conducted to the automatic bed control unit 15 in the boiler control system 16.

The other possibility is that after the sensor heads 11 and 12 the signals are conducted to a filter unit 13 filtering the signals from the sensors to several relatively narrow bands (windows, see above) BAND1 to BANDn which again avoid the disturbance from the thermal radiation emission of hot gases, liquids and particles in the furnace 1. The filtering can take place via mechanical, optical, material related, or electronic devices, or via devices, which are a combination of these. After the filtering the signals are conducted to the image processing control unit 14 for forming a 3D image of the bed which can then be displayed on the screen but the image can also be conducted to the automatic bed control unit 15 in the boiler control system 16.

The sensors are divided into several subsensors whereby each of the subsensors are self-selective in relation to the wavelength range i.e. they receive signals selectively in certain wavelength ranges. Because the sensors have thus different sensor heads for different wavelength ranges the necessary windows are thus achieved. No conventional filtering is needed, instead the filtering is based on comparative filtering by searching the correlation from different 2D sensor images in relation with time and by deciding when the image is correct and forming thus the correct 3D image.

The automatic control unit 15 produces a bed control signal CTRL16 that can be used for control of the liquor injection nozzles, for example so that the bed image steers the movement of the movable nozzle actuators 17 whereby the actuators move the nozzles according to the instructions from the control unit 15. The control unit 15 may be based on simple rules as in basic control units, used for instance to cont-control black liquor temperature before it is sprayed into the furnace, or the control unit 15 may be based on numerical model of the furnace, generated with computational fluid dynamics simulations. The control unit 15 may also utilize neural methods, fuzzy logics or Bayesian algorithms as examples.

The interferences and the char bed are separated in the imaging process by comparing the 3D images from different wavelength areas, and finding the correlations and forming the final 3D image by choosing the relevant images from the images from different wavelength areas.

As said above, the filtering phase where images from different frequencies are compared with each other, taken preferably into consideration Planck's radiation law, takes place before forming the 3D image on the image material. However, the filtering can also take place after forming the 3D image whereby the filtering in this case is made for a 3D image having interference caused by for example burning or radiation of the different gas components in the furnace. As a result of the filtering, which preferably at least partly is comparative comparing the results from different frequency areas, the final 3D image of the char bed is then obtained.

It is obvious to the person skilled in the art that different embodiments of the invention are not limited to the example described above, but that they may be varied within the scope of the enclosed claims.

It is obvious to the person skilled in the art that the described collection of electromagnetic data under several wavelengths, filtering and comparing the collected data, as described above to remove disturbing elements for electromagnetic signals, to gain a 2 dimensional or a 3 dimensional picture can be applied also for easier applications than the char bed of a recovery boiler. Potential applications include for instance heat transfer surfaces and their need for soot blowing, boiler components, ash hoppers, fuel bins etc., in recovery boilers, in other biomass fired boilers, in coal fired boilers. In various types of kilns and ovens the invention can be applied to process follow-up and control, stickiness and build-up control etc.

The invention claimed is:

1. A method for controlling the operation of a recovery boiler or another boiler having a furnace wherein the operation is monitored by monitoring sensors, the method comprising:

said sensors converting the acquired electromagnetic radiation to electrical signals which are conducted to image processing which forms an image of an object, wherein the imaged object includes at least one of a char bed, char, chemicals on at least one of the furnace walls, and deposits on boiler surfaces, and the image is formed based on the data from the sensors;

controlling an operation using the image, wherein the operation includes as least one of burning of the char bed, formation of the char, formation of the chemicals on the furnace walls, and formation of the deposits on the boiler surfaces;

arranging the sensors to produce sensor signals for 3D (three-dimensional) imaging, prior to converting acquired electromagnetic radiation to electrical signals;

wherein the sensor signals are conducted to the image processing unit for forming a 3D image, such as an image of the bed and/or the char and/or the chemicals, and/or its shape describing derivatives, and/or a temperature chart of the bed surface, and that the image processing further comprises a filtering phase wherein the sensor signals or the 3D image are/is filtered in order to avoid the thermal radiation emission of hot gases, liquids and/or particles in the furnace, wherein the sensor signals or the 3D image are/is conducted to a filter unit filtering the signals/images to several relatively narrow bands (BAND1 to BANDn), whereby the final 3D image is obtained by comparative analysis of the sensor signals or the 3D images from the chosen different frequency bands.

2. A method according to claim 1 wherein the sensors are wide range sensors capable of acquiring radiation data in several wavelength ranges, and said ranges include at least one of ultraviolet, visible, IR and millimeter wavelength ranges.

3. A method according to claim 1, wherein the filtering takes place after forming the 3D image whereby the filtering is made for images having interference caused by for example burning or radiation of the different gas components in the furnace, and that as a result of the filtering the final 3D image of the char bed is obtained.

4. A method according to claim 1, wherein the filtering takes place before forming of the 3D image and the sensor signals are conducted to a filter unit filtering the signals from the sensors to several relatively narrow bands (BAND1 to BANDn) of which at least two bands avoid the radiation (light) absorption and emission of hot gases and the compounds in the gases, compared to absorption in strongly affecting bands of H2O, CO and CO2 in these gases.

5. A method according to claim 1, wherein the 3D image, its derivatives and/or the temperature chart are shown as models in the place.

6. A method according to claim 1, wherein the bed is controlled automatically by controlling the spraying of the black liquor using the image.

7. A method according to claim 6, wherein the image is used to steer the movement of at least one movable nozzle actuator whereby the actuator moves the nozzles according to the instructions from a control unit.

8. A method according to claim 1, wherein at least one of the char bed, the char and the chemicals on the furnace walls is controlled automatically by controlling velocities and flows of different air feeds and the air feeds are controlled using the image.

9. A method according to claim 1, wherein the sensors are divided into subsensors selective in relation to the wave length and the subsensors each receive signals selectively in certain wave length ranges.

10. A method according to claim 1, wherein the method is used for minimizing and controlling liquor droplets entering and depositing on the furnace walls, in a lower furnace region below liquor guns and in an upper furnace region extending to a roof of the boiler.

11. A system for controlling the operation of a boiler having a furnace wherein the operation is monitored by monitoring sensors, said system comprising:

said sensors converting acquired electromagnetic radiation to electrical signals which are conducted to an image processing unit which forms an image of an object based on the electrical signals from the sensors, wherein the object includes at least one of a char bed, char, chemicals on a wall of the furnace, and deposits on a surface of the boiler;

a controller controlling at least one operation of the furnace, wherein the operation includes at least one of burning of the char bed, formation of the char, formation of the chemicals on the wall of the furnace, and formation of the deposits on the surface of the boiler, wherein controlling is controlled using the image, wherein the sensors are arranged to produce sensor signals for 3D (three-dimensional) imaging, and the sensor signals are conducted to the image processing unit for forming a 3D image of at least one, of the char bed, the char, the chemicals, and the image processing unit further comprises a filter which processes the sensor signals or the 3D image to avoid the thermal radiation emission in the furnace, wherein filter applies relatively narrow bands (BAND1 to BANDn), whereby the final 3D image is obtained by comparative analysis of the sensor signals or the 3D images from the chosen different frequency bands.

12. A system according to claim 11, wherein the sensors comprise wide range sensors acquiring radiation data in several wavelength ranges, wherein the wavelength ranges include at least one of ultraviolet, visible, IR and millimeter wavelength ranges.

13. A system according to claim 11, wherein the filtering system is arranged after forming the 3D image whereby the filtering is made for images having interference.

14. A system according to claim 11, wherein the filter is arranged before forming of the 3D image and sensor signals are conducted through the narrow bands BAND1 to BANDn of which at least two bands avoid the radiation (light) absorption and emission of hot gases and the compounds in the gases.

15. A system according to claim 11, wherein the 3D image, its derivatives and/or the temperature chart are shown as models in the place.

16. A system according to claim 11, wherein the char bed is controlled automatically by controlling a spray of the black liquor using the image.

17. A system according to claim 11, wherein the bed image is used in steering movable nozzle actuators whereby the actuators move the nozzles according to the instructions from the control unit.

18. A system according to claim 11, wherein the system is used for minimizing and controlling liquor droplets entering and depositing the furnace walls in a lower furnace region below liquor guns and in an upper furnace region extending to a roof of the boiler.

19. A system for controlling the char bed according to claim 11, wherein the sensors include subsensors, and the subsensors include sensor heads detecting different wavelength ranges that are selective such that the subsensors receive signals selectively in certain wave length ranges.

20. A method for controlling operation of a recovery boiler having a furnace wherein the operation is monitored by monitoring image sensors, the method comprising:

arranging the image sensors in the boiler to capture three-dimensional (3D) images of the boiler;

converting electromagnetic radiation captured by the sensors to electrical signals wherein the captured radiation is from at least one of a group consisting of: a char bed, char, chemicals on at least on wall of the furnace, and a deposit on a surface of the boiler;

processing the electrical signals using an image processing unit to form a 3D image of at least one of the char bed, the char, the chemicals on at least on wall of the furnace, and the deposit on the surface of the boiler, wherein the 3D image is representative of at least one of a shape and temperature of the char bed, the char, the chemicals and the deposit;

wherein processing includes filtering the electrical signals or the image to avoid imaging thermal radiation emissions from at least on of hot gases, liquids and particles in the furnace, wherein filtering includes passing the sensor signals or image through a plurality of narrow wavelength bands, and generating a final 3D image based on the filtered sensor signals or the image.

21. A method according to claim 20, wherein the sensors comprise wide range sensors acquiring radiation data in several wavelength ranges.

22. A method according to claim 21 wherein the wide range sensors acquire radiation data in at least one of the wavelength ranges comprising: ultraviolet, visible, IR and millimeter wavelength ranges.

23. A method according to claim 20, wherein the filtering occurs after forming the 3D image and the filtering includes filtering for interference in the image.

24. A method according to claim 23 wherein the interference is caused by at least one of: burning or radiation of the different gas components in the furnace.

25. A method according to claim 20 wherein the filtering occurs before forming of the 3D image and further comprising:

conducting the sensor signals to a filter unit, and filtering the sensor signals to a plurality of narrow bands of which at least two of said narrow bands substantially avoid signals generated by light radiation absorption; by emission of hot gases and by emission of compounds in the hot gases.

26. A method according to claim 25 wherein the at least two of said narrow bands include signals of radiation in wavelengths corresponding to emissions from bands of $H_2O$, CO and $CO_2$ in the hot gases.

27. A method according to claim 20 further comprising presenting a model of the 3D image.

28. A method according to claim 27 further comprising presenting the model in conjunction with a temperature chart of the boiler.

29. A method according to claim 20 further comprising spraying black liquor on the char bed based on image information from the 3D image.

30. A method according to claim 20 further comprising steering a movable nozzle using an actuator, whereby commands to steer the nozzle are generated using the 3D image.

31. A method according to claim 20, further comprising controlling at least one feed of air to the boiler using the 3D image.

32. A method according to claim 20 wherein the sensors are divided into subsensors that are each selective to a different range of wave lengths, and the signals from each of the subsensors corresponds to a different range of wavelengths of the electromagnetic radiation.

33. A method as in claim 20 wherein the boiler is a recovery boiler.

34. A method as in claim 20 further comprising using the 3D image to control liquor droplets entering and depositing the furnace walls.

\* \* \* \* \*